United States Patent [19]

Atkinson et al.

[11] Patent Number: 4,468,469

[45] Date of Patent: Aug. 28, 1984

[54] SUBSTITUTED PHENYLACETIC ACIDS AND SALTS AS TBP BLOCKING AGENTS IN IODOTHYRONINE IMMUNOASSAYS

[75] Inventors: David C. Atkinson; Robert J. Carrico; David L. Morris, all of Elkhart, Ind.

[73] Assignee: Miles Laboratories, Inc., Elkhart, Ind.

[21] Appl. No.: 414,934

[22] Filed: Sep. 3, 1982

Related U.S. Application Data

[63] Continuation-in-part of Ser. No. 318,027, Nov. 4, 1981, abandoned.

[51] Int. Cl.³ .................... G01N 33/52; G01N 33/54
[52] U.S. Cl. ........................................ 436/500; 435/4; 435/7; 436/537; 436/546; 436/804; 436/808; 436/826
[58] Field of Search ............... 436/500, 804, 537, 546, 436/808, 826; 435/4, 7

[56] References Cited

U.S. PATENT DOCUMENTS

| | | | |
|---|---|---|---|
| 3,766,263 | 10/1973 | Godfrey | 760/520 |
| 3,911,096 | 10/1975 | Chopra | 436/500 |
| 3,928,553 | 12/1975 | Hollander | 436/500 |
| 4,018,883 | 4/1977 | Parslow | 436/500 |
| 4,046,870 | 9/1977 | Hertl et al. | 436/500 |
| 4,052,504 | 10/1977 | Hertl et al. | 436/500 |
| 4,057,647 | 11/1977 | Gante et al. | 424/340 |
| 4,066,410 | 1/1978 | Eisentraut | 436/500 |
| 4,108,974 | 8/1978 | Wegfahrt et al. | 436/500 |
| 4,111,656 | 9/1978 | Margherita | 436/500 |
| 4,151,302 | 4/1979 | Gante et al. | 424/317 |
| 4,206,220 | 6/1980 | Sloan | 424/274 |
| 4,225,576 | 9/1980 | Denning et al. | 436/500 |
| 4,307,071 | 12/1981 | Murray et al. | 436/804 |

OTHER PUBLICATIONS

Capper et al., Clinica. Chimica Acta, 112(1981) 77–83.
Ratcliffe et al., The Lancet, Feb. 23, 1980, p. 432.
Humphrey et al., The Lancet, Mar. 1, 1980, pp. 487–488.
Isaacs et al., The Lancet, Feb. 2, 1980, pp. 267–268.

*Primary Examiner*—Christine M. Nucker
*Attorney, Agent, or Firm*—Andrew L. Klawitter

[57] ABSTRACT

An improved immunoassay method, reagent means, and test kit for determining an iodothyronine, e.g., thyroxine (T-4), in a biological fluid, usually serum or plasma, wherein fenclofenac and related phenylacetic acids, or salts thereof, are employed as novel blocking agents for the binding of iodothyronines to thyroxine binding protein (TBP). The present invention is particularly advantageous as applied to homogeneous competitive binding iodothyronine immunoassays wherein a spectrophotometric response is generated in the assay reaction mixture at a wavelength greater than about 300 nm, the blocking agents of the present invention having been found to have no substantial absorbance at wavelengths above 300 nm. Such homogeneous immunoassays include those which employ labels such as fluorescers, enzyme substrates, enzyme prosthetic groups, enzymes, and enzyme inhibitors.

44 Claims, No Drawings

SUBSTITUTED PHENYLACETIC ACIDS AND SALTS AS TBP BLOCKING AGENTS IN IODOTHYRONINE IMMUNOASSAYS

CROSS-REFERENCE TO RELATED APPLICATION

This is a continuation-in-part of application Ser. No. 318,027, filed Nov. 4, 1981, abandoned.

BACKGROUND OF THE INVENTION

1. Field of the Invention

This invention relates to immunoassays for the determination of iodothyronines in biological fluids such as serum or plasma. In particular, the present invention relates to competitive binding immunoassay methods, reagent means, and test kits for determining iodothyronines in unextracted samples of serum or plasma through the use of blocking or dissociating agents for the binding of iodothyronines by thyroxine binding proteins (TBP) present in such samples.

The iodothyronines have the general formula:

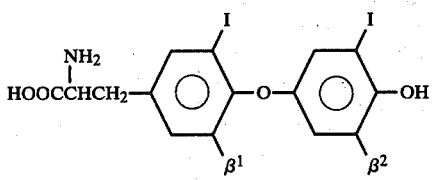

wherein $\beta^1$ and $\beta^2$ are, independently, hydrogen or iodine. The principal iodothyronines of clinical interest are 3,5,3',5'-tetraiodothyronine (thyroxine; T-4) wherein $\beta^1$ and $\beta^2$ are both iodine; 3,5,3'-triiodothyronine (T-3, or simply "triiodothyronine") wherein $\beta^1$ is iodine and $\beta^2$ is hydrogen; 3,3',5'-triiodothyronine ("reverse T-3") wherein $\beta^1$ is hydrogen and $\beta^2$ is iodine; and 3,3'-diiodothyronine wherein $\beta^1$ and $\beta^2$ are both hydrogen. The quantitative determination of the concentration of the various iodothyronines, particularly the hormones T-4 and T-3, in the blood is of important significance in the diagnosis of thyroid disorders.

In the blood, nearly all of the circulating iodothyronines are complexed with various carrier proteins including albumin, thyroxine binding prealbumin and thyroxine binding globulin (TBG), such carrier proteins being generically referred to herein as thyroxine binding protein (TBP). In order to measure the concentration of the total amount of an iodothyronine in a blood sample, such as serum or plasma, the TBP-bound forms must be dissociated to an analytically significant degree and the resulting total free iodothyronine determined. The dissociation of iodothyronines from TBP, particularly TBG, was originally accomplished by an extraction process (U.S. Pat. No. 3,414,383). Under the current state-of-the-art, iodothyronines can be determined by immunoassay in unextracted samples through the use of compounds found empirically to block, and cause dissociation of, TBP binding. In current competitive binding iodothyronine immunoassays, a test sample is combined with reagents including an antibody to the iodothyronine to be determined, a labeled form (e.g., radiolabeled) of such iodothyronine, and one or more TBP blocking agents. The iodothyronine in the sample complexed with TBP is dissociated therefrom and competes with labeled iodothyronine for binding to the antibody. The proportion of labeled iodothyronine that becomes antibody-bound compared to that which remains unbound from antibody is dependent on the total concentration of the iodothyronine in the sample and is measurable in a wide variety of ways depending on the particular immunoassay technique employed.

2. Description of the Prior Art

Various compounds have been discovered as useful TBP blocking agents, including tetrachlorothyronine [Mitsuma et al, J. Clin. Endocrinol. Metab. 33:365 (1971)], diphenylhydantoin [Lieblich and Utiger, J. Clin. Invest. 50:60a (1971)], salicylate [Larson, Metab. 20:976 (1971)], and the various materials disclosed by Hollander (U.S. Pat. No. 3,928,553) and Chopra (U.S. Pat. No. 3,911,096), particularly 8-anilino-1-naphthalenesulfonic acid (ANS). The structures and general properties of the known TBP blocking agents vary over an extremely wide range. The properties critical to operability as a TBP blocking agent in immunoassays, i.e., the ability to sufficiently dissociate iodothyronines from TBP at concentration levels insufficient to cause significant inhibition of the antibody binding reaction, are generally considered unpredictable from purely structural comparisons, although some theories of TBG blocking have been propounded [Brown and Metheany, J. Pharm. Sci. 63:1214 (1974)].

Fenclofenac [2-(2,4-dichlorophenoxy)phenylacetic acid] is a diphenyl ether having antirheumatic activity that has been reported to interfere with thyroid function tests [Lancet 1:267 (Feb. 2, 1980), Lancet 1:432 (Feb. 23, 1980), Lancet 1:487 (Mar. 1, 1980), Capper et al, Clin. Chim. Acta 112:77(1981), and Kurtz et al, Clin. Endocrinol. 15:117(1981)]. Subsequent workers have raised the question whether fenclofenac would be suitable as a TBG blocking agent in thyroid function radioimmunoassays [Ratcliffe et al, Clin. Endocrinol. 13:569(1980)]. Capper et al, supra, also studied the effect of diclofenac [2-(2,6-dichlorophenylamino)phenylacetic acid].

SUMMARY OF THE INVENTION

It has now been found that certain phenylacetic acids and salts are particularly advantageous TBP blocking agents for use in iodothyronine immunoassays. The blocking agent compound is included in the immunoassay reaction mixture at a concentration sufficient to release and block the binding of an analytically significant percentage of TBP-complexed iodothyronine, preferably more than 50% and usually more than 70%, while insufficient to interfere significantly with the binding of antibody with iodothyronine. While the precise concentrations of the blocking agent desired for a particular iodothyronine immunoassay will vary according to the iodothyronine under assay and the immunoassay technique followed, as well as other factors, the compound is normally used in concentrations in the reaction mixture of between about 0.1 millimolar (mM) and about 5 mM, particularly where the iodothyronine involved is thyroxine. The blocking agents of the present invention are added to the assay reaction mixture as the acid or an analytically acceptable salt form thereof, e.g., the sodium, potassium, lithium and ammonium salts.

Certain unexpected properties of the present blocking agents, particularly fenclofenac, make them particularly advantageous for use as TBP blocking agents in homogeneous competitive binding immunoassays wherein a spectrophotometric response, such as a fluorescence emission or light absorption, is generated in the assay reaction mixture at a wavelength greater than about 300 nanometers (nm), and usually less than 700 nm, which response is a function of the concentration of the iodothyronine in the test sample. The present blocking agents have been found to have substantially no absorption at wavelengths greater than 300 nm. Thus, where the spectrophotometric response is a fluorescence emission, or is initiated, although not ultimately expressed, as a fluorescence emission, no quenching of such emission is observed when using the present compounds as the TBP blocking agent, whereas with prior art agents, particularly ANS, a significant quenching can occur resulting in undesirable or unacceptable assay performance characteristics, e.g., decreased sensitivity, reproducibility, precision, etc.

Additionally, fenclofenac in particular will exhibit no substantial inhibitory effect on the catalytic activity of many enzymes at concentrations in which it is an effective TBP blocking agent. Thus, this compound is further advantageous as a TBP blocking agent in homogeneous competitive binding immunoassays wherein the label employed is a participant in an enzymatic reaction, e.g., an enzyme substrate, an enzyme inhibitor, a prosthetic group of an enzyme, a coenzyme, or an enzyme itself, or a fragment thereof. Prior art TBP blocking agents, particularly ANS, can cause significant inhibition of enzyme reactions resulting again in decreased assay performance.

Therefore, the present phenylacetic acids and salts find novel use as TBP blocking agents in immunoassays in general, and are particularly advantageous when applied to spectrophotometric homogeneous immunoassays, especially, in the case of fenclofenac, those in which the label employed is a participant in an enzyme-catalyzed reaction. The present invention also provides reagent means for performing the novel immunoassays, particularly in the form of test kits as commonly used in clinical laboratories.

DESCRIPTION OF THE PREFERRED EMBODIMENTS

The phenylacetic acids of the present invention are generally of the formula:

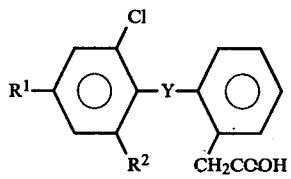

wherein Y is O or NH and one of $R^1$ and $R^2$ is chloro and the other is hydrogen, and have been found to have unexpected features as TBP blocking agents. Fenclofenac (Y=O and $R^1$=Cl) has been found to be especially advantageous in this respect, particularly in homogeneous iodothyronine immunoassays. Another compound of interest is diclofenac (Y=NH and $R^2$=Cl). It will, however, be evident to one of ordinary skill in the art that various modifications can be made to the basic diphenyl structure of the formula above without departing from the present inventive concept. Analogs possessing the advantageous TBP blocking agent features of the present invention will be considered as equivalents for the purposes of the claims hereof. For example, without limitation, the oxy or imino linking functionality may be replaced with a suitable analogous linker, including such groups as thio, methylene, and keto. Further, the dichloro substituents may be replaced by single or multiple substituents on either of the phenyl rings, such substituents being selected from halo, particularly chloro, bromo, and iodo; alkyl, usually lower alkyl ($C_{1-4}$), e.g., methyl and ethyl; and alkoxy, usually lower alkoxy, e.g., methoxy and ethoxy. Also, the acetate substituent may be representative of a series of acid groups, e.g, carboxylic and sulfonic acids and their alkyl homologs, particularly the lower alkanoic homologs, and such groups may be bonded to a phenyl ring at either the meta or para position in addition to the ortho position in the formula. See also U.S. Pat. No. 3,766,263.

The present invention has applicability to iodothyronine immunoassays in general. For the purposes hereof, an immunoassay will be understood to mean any assay based on antigen-antibody interactions and antibody will be understood to mean whole conventional or monoclonal antibody (e.g., of the IgG, IgM, IgA, etc., types) or an effective fragment thereof (e.g., Fab, F(ab'), etc. fragments of IgG). The most common type of immunoassay to which the present invention will be advantageously applied is the competitive binding immunoassay. In such an immunoassay for determining an iodothyronine, a test sample of a body fluid, usually serum or plasma, is combined with an antibody to the iodothyronine under assay, a labeled form of the iodothyronine, and a blocking agent for TBP binding. The proportion of labeled iodothyronine that becomes bound to the antibody in competition with any iodothyronine in the sample compared to that which remains unbound is related to the concentration of the iodothyronine in the sample.

Both homogeneous and heterogeneous immunoassay techniques may be followed, the former being particularly preferred. In heterogeneous immunoassays, the antibody-bound form of the labeled iodothyronine is physically separated, as is known in the art, from the unbound form and the label measured in one or the other of the separated phases. Various different labels are known for use in heterogeneous immunoassays, including radioactive isotopes (e.g., U.S. Pat. Nos. 4,111,656 and 3,911,096), fluorescers (e.g., U.S. Pat. Nos. 4,201,763; 4,171,311; 4,133,639; and 3,992,631), enzymes (e.g., U.S. Pat. No. 3,654,090), and so forth. In radioimmunoassays for iodothyronines it is particularly advantageous to use radioactive iodine as the label, substituting same for one of the native iodines in the iodothyronine.

In homogeneous immunoassays, which are particularly preferred in the present invention, the antibody-bound form of the labeled iodothyronine expresses a different property from the unbound form and thus the separation step required in heterogeneous assays can be avoided. A wide variety of homogeneous immunoassay techniques are known in the art. Particularly preferred are those wherein the label which is chemically conjugated to the iodothyronine is an enzyme, or an enzyme fragment, e.g., a prosthetic group, or is a participant in an enzyme-catalyzed reaction, e.g., a substrate, a coenzyme, an inhibitor, an activator, or the like.

The present invention is particularly applicable to homogeneous competitive binding immunoassays wherein a spectrophotometric response is generated in the assay reaction mixture at a wavelength greater than about 300 nm, and usually less than 700 nm, which response is indicative of the iodothyronine concentration in the test sample. The present blocking agents have been found to have substantially no absorption at such wavelengths. By spectrophotometric response is meant an optically detectable signal, usually measured at a selected wavelength or wavelengths. Exemplary of such signals are light emissions, e.g., chemiluminescence (including bioluminescence) and fluorescence, and light absorptions or reflections, e.g., color changes or formations, and measurable absorbance or reflectance changes in the visible spectrum. The following are examples of such assay types:

1. Fluorescence quenching or enhancement

The labeled conjugate in this system is composed, in its label portion, of a fluorescer whose fluorescence is quenched or enhanced in some measurable degree when the labeled iodothyronine conjugate is bound by antibody. The fluorescent label is usually measured directly, with its fluorescence being the detectable signal. Assay systems of this type are described in U.S. Pat. Nos. 4,160,016 and 3,940,475; in U.K. Pat. Spec. 1,583,869; and in *J. Clin. Path.* 30:526 (1977).

2. Fluorescence polarization

The label in this system is also a fluorescer; however, the affected characteristic is polarization of fluorescence due to binding of the labeled conjugate by antibody. Assay systems of this type are described in *J. Exp. Med.* 122:1029(1975).

3. Enzyme substrate-labeled techniques

In this system, the label is selected so that the labeled conjugate is a substrate for an enzyme and the ability of the enzyme to act on the substrate-labeled conjugate is affected, either in a positive or negative sense, by binding of the labeled conjugate with antibody. Action of the enzyme on the substrate-labeled conjugate produces a product that is distinguishable in some feature, usually a chemical or physical feature such as chemical reactivity in an indicator reaction or such as a photometric character, e.g., fluorescence or light absorption (color). Assay systems of this type are described in general terms in commonly assigned, copending application Ser. No. 894,836, filed Apr. 10, 1978 (corresponding to U.K. Pat. Spec. No. 1,552,607); and in *Anal. Chem.* 48:1933(1976), *Anal. Biochem.* 77:55(1977) and *Clin. Chem.* 23:1402(1977). In such enzyme substrate-labeled techniques, the labeled conjugate, e.g., a substrate-analyte conjugate, will have the property that it can be acted upon by an enzyme, by cleavage or modification, to produce a product having a detectable property which distinguishes it from the conjugate. For example, the conjugate may be nonfluorescent under assay conditions but upon reaction with enzyme a fluorescent product is produced.

Various fluorogenic substrate-labeled conjugates are evident for use in such techniques. For example, the labeled conjugate may be of the formula:

G—D—R—L wherein G is a cleavable group such as phosphate, carboxylate, or glycone, D is a fluorogenic dye moiety which upon removal of G yields a fluorescent product, e.g., D can be umbelliferone, fluorescein, rhodamine, and their derivatives, R is a linking group and L is the binding component, usually the analyte (e.g., an iodothyronine) or a derivative thereof. Enzymatic cleavage (e.g., by phosphatase, carboxylase, glycosidase, etc.) of the labeled conjugate is affected by binding, such as by antibody, to the L portion of the conjugate. See U.S. Pat. No. 4,279,992. A particularly preferred substrate-labeled assay scheme employs a labeled conjugate of the type:

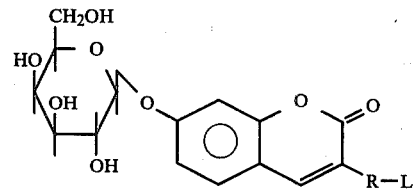

wherein R is a linking group and L is the binding component, e.g., the analyte or analog thereof, whereby the ability of the enzyme β-galactosidase to cleave the conjugate yielding a product distinguishable by its fluorescence is inhibited by binding of the conjugate with antibody.

Other useful substrate-labeled conjugates are those of the formula:

D—R—L wherein R is an enzyme cleavable linking group, e.g., phosphate, carboxylate, and the like, L is the binding component as above, and D is a fluorogenic dye moiety as above which upon cleavage of R releases a fluorescent indicator. A particularly preferred technique employs a labeled conjugate of the type:

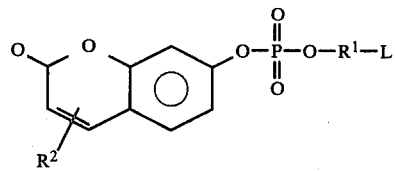

wherein $R^1$ is a bond or chain linking the labeled component L to the cleavable phosphate group and $R^2$ is hydrogen or a substituent group such as lower alkyl, e.g., methyl and ethyl, N-alkylamido or N-(hydroxy-substituted lower alkyl)amido, e.g., —CONH—CH$_2$—)$_n$OH wherein n=2-6 (see U.S. Pat. No. 4,273,715). The umbelliferone residue may bear other or additional substituents [see *Anal. Chem.* 40:803(1968)]. Cleavage by phosphodiesterase is affected by binding of antibody to the L portion of the conjugate.

4. Energy transfer

In this system, the label is one member of an energy transfer donor-acceptor pair and the antibody is conjugated with the other of such pair. Thus, when the labeled conjugate is bound by antibody, the energy expression of the donor component of the pair is altered by transfer to the acceptor component. Usually, the donor is a fluorescer and the acceptor is a quencher therefor, which quencher may or may not be a fluorescer as well. In such embodiment, the detectable signal is fluorescence, but other detectant systems are possible also. Such assay systems are described in U.S. Pat. Nos. 3,996,345; 4,174,384; and 4,199,559 and in U.K. Pat. Spec. No. 2,018,424.

5. Chemically-excited fluorescence

In this system, the label is again a fluorescer, however, the ability of the fluorescer label to be chemically excited to an energy state at which it fluoresces is affected by binding of the labeled conjugate with antibody. Chemical excitation of the label is usually accomplished by exposure of the fluorescer label to a high energy compound formed in situ. Assay systems of this type are described in commonly owned U.S. Pat. No. 4,238,195.

6. Double antibody steric hindrance

Another assay system is the double antibody immunoassay system described in U.S. Pat. Nos. 3,935,074 and 3,998,943. The labeled conjugate comprises two epitopes, one of which participates in the immunological reaction with the ligand and anti-ligand antibody and the other of which is bindable by a second antibody, with the restriction that the two antibodies are hindered from binding to the labeled conjugate simultaneously. The second epitope can be a fluorescent substance whose fluorescence is quenched by the second antibody binding, or may participate in an ancillary competitive binding reaction with a labeled form of the second epitope for binding to the second antibody. Various detectant systems are possible in such a system as described in the aforementioned patents. Related assay systems are described in U.S. Pat. Nos. 4,130,462 and 4,161,515 and in U.K. Pat. Spec. No. 1,560,852.

7. Prosthetic group-labeled techniques

In this system, the label is a prosthetic group of an enzyme, and the ability of a catalytically inactive apoenzyme to combine with the prosthetic group label to form an active enzyme (holoenzyme) is affected by binding of the labeled conjugate with antibody. Resulting holoenzyme activity is measurable by conventional detectant systems to yield an ultimate detectable signal. Assay systems of this type are described in commonly owned U.S. Pat. No. 4,238,565. A particularly preferred prosthetic group-labeled assay scheme employs flavin adenine dinucleotide (FAD) as the label and apoglucose oxidase as the apoenzyme. Resulting glucose oxidase activity is measurable by a colorimetric detectant system comprising glucose, peroxidase, and an indicator system which produces a color change in response to hydrogen peroxide. Fluorometric detection of hydrogen peroxide is also possible using an appropriate fluorogenic substrate.

8. Coenzyme-labeled techniques

The labeled conjugate in this system is composed, in its label portion, of a coenzyme-active functionality, and the ability of such coenzyme label to participate in an enzymatic reaction is affected by binding of the labeled conjugate with antibody. The rate of the resulting enzymatic reaction is measurable by conventional detectant systems to yield an ultimately detect able signal. Assay systems of this type are described in commonly assigned, copending application Ser. No. 894,836, filed Apr. 10, 1978 (corresponding to U.K. Pat. Spec. No. 1,552,607); and in *Anal. Biochem.* 72:271(1976), *Anal. Biochem.* 72:283(1976) and *Anal. Biochem.* 76:95 (1976).

9. Enzyme modulator-labeled techniques

The labeled conjugate in this system is composed, in its label portion, of an enzyme modulating functionality such as an enzyme inhibitor or stimulator, and the ability of such modulator label to modulate the activity of an enzyme is affected by binding of the labeled conjugate with antibody. The rate of the resulting enzymatic reaction is measurable by conventional detectant systems to yield an ultimately detectable signal. Assay systems of this type are described in U.S. Pat. Nos. 4,134,792 and 4,273,866. Particularly preferred is the use of methotrexate as the label with dihydrofolate reductase as the modulated enzyme.

10. Enzyme-labeled techniques

In this system, the label is an enzyme and the activity of the enzyme label is affected by binding of the labeled conjugate with antibody. Resulting enzyme activity is measurable by conventional detectant systems to yield an ultimately detectable signal, e.g., absorption or fluorescence. Assay systems of this type are described in U.S. Pat. Nos. 3,817,837 and 4,043,872.

Other homogeneous competitive binding immunoassay techniques can be followed without departing from the present inventive concept.

Since fenclofenac in particular also will have insubstantial inhibitory effect on the catalytic activity of many enzymes at concentrations in which it is effective as a TBP blocking agent, the present invention is further advantageous in homogeneous immunoassays involving enzymatic reactions. Such assays include the enzyme substrate-labeled, prosthetic group-labeled, coenzyme-labeled, enzyme modulator-labeled, and enzyme-labeled techniques described above. By insubstantial inhibitory effect on enzymatic activity is meant that the rate of catalysis is not decreased more than about 70%, more usually less than 50%, and preferably less than 30%.

The biological fluid to be tested may be any in which the iodothyronine(s) of interest may be undesirably associated with binding proteins. In the usual situation, the biological fluid is a blood sample such as whole blood, serum or plasma.

The reagent means of the present invention comprises all of the essential chemical elements required to conduct a desired iodothyronine immunoassay method encompassed by the present invention. The reagent means is presented in a commercially packaged form, as a composition or admixture where the compatibility of the reagents will allow, in a test device configuration, or as a test kit, i.e., a packaged combination of one or more containers holding the necessary reagents. Included in the reagent means are the reagents appropriate for the binding reaction system desired and having a compound of the present invention, e.g., fenclofenac, as a TBP blocking agent. Such binding reaction reagents usually include, in addition to the blocking agent, a labeled iodothyronine conjugate, antibody to the iodothyronine under assay, and possibly other TBP blocking agents as may be desired. Of course, the reagent means can include other materials as are known in the art and which may be desirable from a commercial and user standpoint, such as buffers, diluents, standards, and so forth. Particularly preferred is a test kit for the homogeneous competitive binding immunoassay of the present invention comprising (a) an antibody to the iodothyronine to be determined, (b) a labeled iodothyronine conjugate which has a detectable property which is altered when bound with the antibody and (c) a compound of the present invention as a TBP blocking agent. The specific label used will depend on the technique followed, as described hereinabove. Also preferred is a test device comprising a reagent composition including an iodothyronine antibody, a labeled iodothyronine conjugate which has a detectable property which is altered when bound with the antibody, and a compound of the present invention as a TBP blocking agent, and a solid carrier member incorporated with the reagent composition. The various forms of such test device are described in U.S. patent application Ser. No. 202,378, filed Oct. 30, 1980, which is incorporated herein by reference.

The present invention will now be illustrated, but is not intended to be limited, by the following examples.

EXAMPLES

I. Dissociation of Thyroxine from Human Serum with Fenclofenac and Diclofenac Approximately 3 milliliters (ml) of human serum was allowed to equilibrate with radioactive iodine-labeled thyroxine ($^{125}$I-thyroxine obtained from Amersham-Searle, Arlington Heights, Ill., USA) for about 8 hours.

Then 100 microliter ($\mu$l) aliquots of this serum were combined with 300 $\mu$l aliquots of 0.1 molar (M) sodium phosphate buffer, pH 6.5, containing various concentrations of fenclofenac (British Pat. No. 1,308,327; example 6). Then 180 $\mu$l aliquots of each of these mixtures were applied to 2 ml columns of Sephadex LH-20 (Pharmacia Fine Chemicals, Piscataway, N.J. USA) equilibrated with 0.1M sodium phosphate buffer, pH 6.5. The radioactivity on the columns was measured and the columns were washed with 5 ml of the buffer. The radioactivity of each column was measured again and the results (shown below in Table 1) used as estimates of thyroxine dissociated from serum proteins.

TABLE 1

| Fenclofenac (mM) | Percent Thyroxine Dissociated |
|---|---|
| 0 | 19 |
| 0.25 | 50 |
| 0.50 | 72 |
| 1.0 | 79 |
| 2.0 | 98 |
| 5.0 | 100 |

A second experiment was run to compare the dissociation characteristics of fenclofenac and diclofenac. Radioactive iodine labeled thyroxine ($^{125}$I-thyroxine obtained from Amersham-Searle, Arlington Heights, IL, USA) was equilibrated with 5 ml of normal human serum for 48 hours at 4° C. Aliquots of this serum (100 $\mu$l) were added to 300 $\mu$l of 0.1M sodium phosphate, pH 7.0, containing various concentrations of fenclofenac or diclofenac (see Example XI) to give the final concentrations given in Table 1A. After 5 minutes of incubation at room temperature, a 165 $\mu$l aliquot was applied to a Sephadex ® column from a Seralute ® thyroxine assay kit (Miles Laboratories, Inc., Ames Division, Elkhart, IN, USA), which had been equilibrated with 0.1M sodium phosphate, pH 7.0. The total radioactivity applied to the columns was measured and the undissociated material was washed through the column with 3 ml of buffer. The columns were counted to determine the percentage of thyroxine dissociated from the serum proteins.

TABLE 1A

| Dissociating Agent Concentration (mM) | Percent Dissociated (Fenclofenac) | Percent Dissociated (Diclofenac) |
|---|---|---|
| 0 | 9 | 9 |
| 0.25 | 40 | 48 |
| 0.50 | 61 | 61 |
| 1.00 | 71 | 73 |
| 2.00 | 75 | 77 |
| 4.00 | 79 | 80 |
| 8.00 | 81 | 82 |

Therefore, 0.25 mM fenclofenac in an iodothyronine immunoassay reaction mixture can be expected to release and block the binding of about 40–50% of the protein-bound iodothyronine, and 0.50 mM about 60–70%. The second study showed that both dissociating agents are equally effective in dissociating iodothyronine from serum proteins in an immunoassay reaction.

II. Effect of Fenclofenac on the Binding of Thyroxine with Antibody

A series of antibody binding reactions were set up in 0.1M sodium phosphate buffer, pH 6.5, to give final volumes of 0.6 ml containing various concentrations of fenclofenac. Each reaction contained $^{125}$I-thyroxine, 20 $\mu$l of normal rabbit immunoglobulin, and 2 $\mu$l of antibody to thyroxine. The mixtures were incubated at room temperature for about 3 hours and then 400 $\mu$l of 50% (w/v) polyethyleneglycol was added. The precipitated proteins were collected by centrifugation and the radioactivity in each precipitate was measured. The results are shown in Table 2 as percent of the radioactivity in the precipitate without fenclofenac.

TABLE 2

| Fenclofenac (mM) | Percent $^{125}$I-Thyroxine in Precipitate |
|---|---|
| 0 | 100 |
| 0.2 | 97 |
| 0.5 | 80 |
| 1.0 | 69 |
| 2.5 | 61 |
| 5.0 | 43 |

The data indicate that concentrations of fenclofenac below about 5 mM inhibit the antibody binding reaction only about 50% and below about 2.5 mM only about 40%. Based on this data and that of Example I, preferred fenclofenac concentrations in a thyroxine immunoassay reaction mixture would be in the range of 0.25–1.0 mM.

III. Radioimmunoassay for Thyroxine

A radioimmunoassay for thyroxine in serum was conducted using fenclofenac as the TBP blocking agent. Serum standards in 100 $\mu$l aliquots containing known concentrations of thyroxine were combined with 290 $\mu$l of 0.1M sodium phosphate buffer, pH 6.5, an amount of fenclofenac to give a concentration of 0.67 mM in the final assay mixture, 2 $\mu$l of rabbit antibody to thyroxine, and a fixed amount of $^{125}$I-thyroxine (approximately 34,000 counts per minute per 100 $\mu$l in the final volume). After incubation at room temperature for 2 hours, 400 $\mu$l of 50% (w/v) polyethyleneglycol was added and the resulting precipitates collected by centrifugation. The radioactivity of each precipitate was then measured. The results are shown in Table 3 ($\mu$g/dl is micrograms per deciliter).

TABLE 3

| Thyroxine (μg/dl) | Counts per Minute in Precipitate |
| --- | --- |
| 0 | 23,700 |
| 1.0 | 21,800 |
| 2.5 | 17,300 |
| 5.0 | 14,400 |
| 10.0 | 10,000 |
| 20.0 | 7,500 |

The data indicate that as the thyroxine level in the serum sample increased, the amount of labeled thyroxine bound to antibody decreased. It was accordingly demonstrated that fenclofenac can be used effectively in competitive binding immunoassays for the iodothyronine thyroxine in serum.

IV. Optical Absorption Spectra of Fenclofenac and Diclofenac

A 50 mM solution of fenclofenac in dilute sodium hydroxide solution was prepared and observed to have no visible color. The optical absorption spectrum of a 0.5 mM solution in 0.1M sodium phosphate buffer, pH 6.5, was recorded and showed no significant absorption above 300 nanometers (nm). Accordingly, fenclofenac could have no significant effect on spectrophotometric signals generated above such wavelength.

In contrast, the conventionally used blocking agent ANS has a significant absorption above 300 nm. A 50 μM solution of ANS in 0.1M phosphate buffer, pH 7.0, showed a broad absorption band from 300–400 nm with a peak of 0.5 at about 350 nm. Thus, ANS gives significant absorption at very low concentrations, concentrations far below those at which ANS is normally used as a blocking agent (around 1 mM).

In a second study, solutions of fenclofenac and diclofenac were prepared by dissolving them in 0.1M sodium hydroxide and the spectra were made with a Bausch & Lomb Spectronic 2000 dual beam scanning spectrophotometer.

TABLE 3A

| | Fenclofenac* | Diclofenac* |
| --- | --- | --- |
| λmax NaOH | 275 269 | 275 |
| ε max | 2.06 × 10³ 2.05 × 10³ | 11.8 × 10³ |
| λmin NaOH | 257 | 248 |
| ε min | 1.52 × 10³ | 6.4 × 10³ |

*Wavelength in nanometers and extinction coefficient is $M^{-1} \cdot cm^{-1}$.

While both compounds have a near-UV absorbance spectrum, neither of them have any absorbance above 320 nm. Neither compound would contribute any interference with spectrophotometric generated signals above this wavelength.

V. Effect of Fenclofenac on the Activation of Apoglucose Oxidase by FAD-labeled Conjugates A series of apoenzyme reactivation measurements were set up with different concentrations of fenclofenac. The assays were performed at 37° C. and the final reagent concentrations in 0.1M phosphate buffer, pH 7.0, were 1.0 nanomolar (nM) FAD-labeled conjugate (an FAD-theophylline conjugate as described in U.S. Pat. No. 4,238,565), 50 nM apoglucose oxidase (U.S. Pat. No. 4,268,631), 2.5 μl/ml anti(glucose oxidase) antiserum, 2 mM sodium dichlorohydroxybenzene sulfonate (DHSA), 0.2 mM 4-aminoantipyrine, 0.1M glucose, 20 μg/ml peroxidase, and 0.1% (w/v) bovine serum albumin. The apoenzyme and anti(glucose oxidase) were preincubated and the reaction then started by simultaneously mixing in the other reagents. The reaction mixtures were incubated for 5 minutes and then absorbance at 520 nm read. The results shown in Table 4 relate fenclofenac concentration to the generation of active glucose oxidase.

TABLE 4

| Fenclofenac (mM) | Percent Apoglucose Oxidase Activity |
| --- | --- |
| 0 | 100 |
| 0.5 | 81 |
| 1.0 | 66 |
| 1.5 | 61 |
| 2.0 | 64 |
| 2.5 | 47 |

The data indicate that fenclofenac concentrations below 2.5 mM permit the recombination of apoglucose oxidase and FAD-labeled conjugates to proceed at a rate sufficient for use of a prosthetic group-labeled immunoassay (U.S. Pat. No. 4,238,565).

For the purposes of comparison, a series of apoenzyme reactivation measurements were set up with different concentrations of the conventionally used blocking agent ANS. The following reagents were prepared:

Reagent A
  0.105M potassium phosphate buffer, pH 7.0
  0.105M Glucose
  2.2 mM DHSA
  21 μg/ml peroxidase
  1.1% (w:v) bovine serum albumin
  5.26 nM FAD-labeled conjugate, supra Reagent B
  4 μM apoglucose oxidase, supra
  30% (w:v) glycerol
  50 mM phosphate buffer, pH 7.0
  8 mM 4-aminoantipyrine ANS was dissolved directly into separate aliquots of Reagent A in the concentrations shown in Table 5. Apoenzyme activity was determined by placing 50 μl of Reagent B in a cuvette and starting the reaction by addition of 1.90 ml of Reagent A. The assay reactions were incubated for 10 minutes at room temperature and the absorbances at 520 nm recorded. The results are shown in Table 5.

TABLE 5

| ANS (mM) | Percent Apoglucose Oxidase Activity |
| --- | --- |
| 0 | 100 |
| 0.1 | 64 |
| 0.2 | 46 |
| 0.5 | 13 |
| 1.0 | 0 |

The data show that ANS concentrations above about 1.0 mM totally inhibit the recombination reaction. Since ANS concentrations around this concentration are required for blocking agent purposes, ANS could not be used in the immunoassay.

In a second study, the effect of fenclofenac on the activation of apoglucose oxidase by an FAD-iodothyronine (T-4) conjugate was investigated. The activation of apoglucose oxidase was set up with different concentrations of fenclofenac and performed at 37° C. To two sets of assays containing 96 mM sodium phosphate, pH 7.0, 95 mM glucose, 1.0 mM sodium dichlorohydroxybenzene sulfonate (DHSA), 19 μg/ml peroxidase and various concentrations of sodium fenclofenac were added apoglucose oxidase, 4-aminoantipyrine, and anti-(glucose oxidase) at final concentrations of 100 nM, 100 μM, 5 μl/ml respectively or 2.1 nM final concentration of an FAD-thyroxine conjugate. After preincubating the assay media for 5 min at 37° C. the FAD-thyroxine conjugate or the apoglucose oxidase reagent was added to the appropriate assay set. The absorbance at 520 nm was recorded after a 330 second incubation. The data are presented as a percentage of the absorbance recorded when no fenclofenac is present.

TABLE 4A

| Fenclofenac (mM) | Started with Apoenzyme Addition | Started with Conjugate Addition |
|---|---|---|
| 0 | 100 | 100 |
| 0.16 | 100 | 97 |
| 0.31 | 98 | 92 |
| 0.63 | 97 | 94 |
| 1.25 | 93 | 95 |
| 2.5 | 90 | 85 |
| 5.0 | 78 | 74 |
| 10.0 | 53 | 54 |

The colorimetric response was diminished by only 8-10% at about 2 mM fenclofenac when an FAD-thyroxine conjugate was used to activate the apoglucose oxidase under the conditions employed for an actual iodothyronine immunoassay.

VI. Studies on Fluorescence Quenching by Fenclofenac

Fluorescence measurements were conducted in 50 mM Bicine buffer (N,N-bis-(2-hydroxyethyl)glycine, Calbiochem-Behring, LaJolla, Calif., USA), pH 8.3, using an Aminco Bowman Fluorometer (American Instruments, Silver Springs, Md., USA), excitation set at 400 nm and emission at 450 nm, which are the fluorescence conditions for the β-galactosyl-umbelliferone enzyme substrate-labeled fluorescent immunoassay (SLFIA) described in U.S. Pat. No. 4,279,992. Under these conditions, 10 mM fenclofenac did not exhibit any fluorescence.

Quenching studies were performed by measuring the fluorescence of a 1.3 μM solution of 2-[7-hydroxy-3-carboxamidocoumarin]ethanol (U.S. Pat. No. 4,273,715) in the presence of various levels of fenclofenac. The ratios of observed fluorescence (F) to fluorescence in the absence of fenclofenac (Fo) versus fenclofenac concentration were calculated and are presented in Table 6.

TABLE 6

| Fenclofenac (mM) | F/Fo |
|---|---|
| 0 | 1.00 |
| 0.2 | 1.00 |
| 1.0 | 1.01 |
| 2.0 | 1.00 |
| 5.0 | 1.00 |
| 10. | 1.02 |

The data indicate that fenclofenac exhibits essentially no quenching of the umbelliferone fluorescer used in the SLFIA technique and accordingly is well suited for use as a TBP blocking agent in such homogeneous immunoassay technique (U.S. Pat. No. 4,279,992).

VII. Effect of Fenclofenac on the Activity of the Enzyme Dihydrofolate Reductase Assay mixtures were prepared to contain various concentrations of fenclofenac and, in a 1 ml final volume at 37° C., 0.3 mM thiazoyl blue, 0.115M dihydrofolate, 0.5 mM NADPH, and 0.012 Units/ml of dihydrofolate reductase. The absorbance of each reaction mixture at 560 nm was read over a 10 minute incubation period at 37° C. The results are given in Table 7.

TABLE 7

| Fenclofenac (mM) | Absorbance Change Over 10 Minutes |
|---|---|
| 0 | 0.360 |
| 0.1 | 0.359 |
| 0.2 | 0.365 |
| 0.5 | 0.355 |
| 1.0 | 0.332 |
| 2.5 | 0.273 |
| 5.0 | 0.118 |

The data indicate that fenclofenac did not give substantial inhibition of enzyme activity at concentrations below 1.0 mM which are effective in dissociating thyroxine from serum proteins and accordingly is well suited for use as a TBP blocking agent in enzyme modulator-labeled homogeneous immunoassays (U.S. Pat. No. 4,134,792).

VIII. Enzyme Inhibitor-Labeled Immunoassay for Thyroxine

An enzyme inhibitor-labeled immunoassay (U.S. Pat. No. 4,134,792) for thyroxine in serum was conducted using fenclofenac as the TBP blocking agent. Serum standards in 40 μl aliquots containing known concentrations of thyroxine were combined with 0.2 ml of an antibody reagent consisting of 21 μl rabbit antiserum to thyroxine in 1 ml of 0.1M sodium phosphate buffer, pH 6.5, containing 0.3M potassium chloride, 0.05% sodium azide, and 0.5 mM fencolfenac. After a 30 second incubation, to each mixture was added 0.2 ml of a conjugate reagent consisting of 0.63 mg/ml NADPH (0.65 mM), 0.0175 μM of a methotrexate-thyroxine conjugate [prepared as described in the U.S. patent application filed on even date herewith, assigned to the present assignee, entitled "Methotrexate-Labeled Iodothyronine Conjugates Ser. No. 318,028, which application is incorporated herein by reference] in 10 mM sodium carbonate buffer, pH 9.5. After another 30 second incubation, to each mixture was added 0.2 ml of an enzyme reagent consisting of dihydrofolate reductase at a concentration of 27.5 nM methotrexate binding sites in 0.1M Tris-HCl buffer (tris-(hydroxymethyl)aminomethane hydrochloric salt, Calbiochem-Behring, La Jolla, Calif., USA), pH 8.5, containing 0.5% (w:v) gelatin and 0.005% (w:v) chlorhexidine (Sigma Chemical, St. Louis, Mo., USA). After a further 5 minute incubation, to each mixture was added 50 μl of 2.5 mM dihydrofolate in 0.1M Tris.HCl, pH 8.5. Forty-five (45) seconds later, the absorbance of each solution at 340 nm was read over a 1 minute period. The results are given in Table 8.

TABLE 8

| Thyroxine (μg/dL) | Absorbance Change per Minute |
|---|---|
| 0 | 0.1682 |
| 1.0 | 0.1659 |
| 2.5 | 0.1648 |
| 10. | 0.1571 |

TABLE 8-continued

| Thyroxine (μg/dL) | Absorbance Change per Minute |
|---|---|
| 20. | 0.1498 |

Accordingly, as the thyroxine level in the serum sample increased, the amount of enzyme inhibition by the inhibitor-thyroxine conjugate increased. Fenclofenac did not substantially interfere with either the spectrophotometric response at 340 nm or the enzymatic reaction.

VIII. Enzyme Substrate-Labeled Immunoassay for Thyroxine

A. Synthesis of labeled conjugate-5-(thyroxinamido) pentyl, 4-methylumbelliferone, hydrogen phosphate

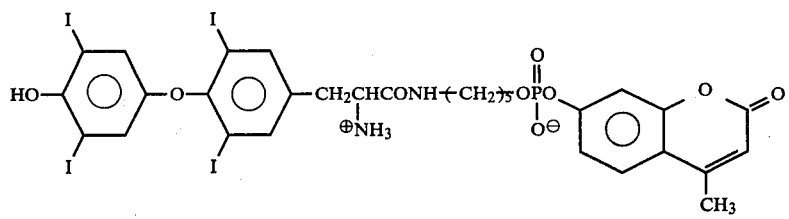

A solution of 8.73 g (10 mmol) of N-trifluoroacetyl L-thyroxine, 1.133 g (11 mmol) of 5-amino-1-pentanol, and 2.7 g (20 mmol) of 1-hydroxybenzotriazole in 125 ml of dry dimethylformamide (DMF) was cooled to −5° C. while stirring under argon. To this was added 2.28 g (11 mmol) of dicyclohexylcarbodiimide. The cooling bath was removed and the reaction allowed to come to room temperature and stir for 3 hours. The solvent was removed in vacuo. The residue was taken up in 250 ml of ethyl acetate, filtered, and washed with 150 ml of saturated aqueous sodium bicarbonate solution and 5% aqueous citric acid solution. This residue was purified by preparative liquid chromatography in a slica gel column eluting with 5:1 (v/v) methylene chloride:acetone. This gave 6.5 g (67% yield) of the N-(5-hydroxypentyl)amide of N-trifluoroacetylthyroxine as a white solid, mp 202°–203° C.

Analysis: Calculated for $C_{22}H_{21}F_3I_4N_2O_5$: C, 27.58; H, 2.21; N, 2.92. Found: C, 27.89; H, 2.18; N, 3.36.

The N-(5-hydroxypentyl) amide (5.75 g, 6 mmol) and 2.01 g (6 mmol) of the pyridinine salt of 4-methylumbelliferone-monophosphate were suspended in 75 ml of dry DMF. The mixture was concentrated to about 25 ml in volume on a rotary evaporator attached to a vacuum pump. An additional 20 ml of dry DMF was added followed by 30 ml of dry pyridine. Solid dicyclohexylcarbodiimide (2.48 g, 12 mmol) was then added and the reaction stirred under argon at room temperature for 24 hours. Solvent was removed under vacuum and the residue stirred with 300 ml of 0.1M aqueous triethylammonium bicarbonate for 1 hour. The white precipitate was filtered and then stirred for 30 minutes in 300 ml of ether and filtered. This left 8 g of the desired product contaminated with dicyclohexyl urea. This residue (1.6 g) was taken up in methanol (some insoluble material was removed by filtration) and chromatographed on Sephadex LH-20 (60 cm × 5 cm) eluting with methanol. The flow rate was 0.5 ml/minute and 10 ml fractions were collected.

Fractions 69 through 76 were pooled and evaporated to give, as a white glassy solid, 390 mg of 5-[N-(trifluoroacetamido) thyroxinamido]pentyl, 4-methyl hydrogen phosphate, triethylammonium salt.

Analysis: Calculated for $C_{38}H_{43}F_3I_4PN_3O_{10}$: C, 35.18; H, 3.34; N, 3.24. Found: C, 37.01; H, 3.63; N, 3.36.

A 200 mg portion of the N-trifluoroacetamido-protected phosphodiester was dissolved in 50% aqueous methanol, pH 12, for 3 hours. The reaction was quenched with 0.5 ml of acetic acid and then concentrated to dryness under vacuum. The residue was taken up in methanol containing a little ammonium hydroxide, 2.5 g of silica gel added, and solvent removed. The impregnated adsorbent was placed atop a column of 25 g of silica gel made up in 10:5:1 (v/v/v) chloroform:methanol:concentrated ammonium hydroxide. The column was eluted with this solvent and 9 ml fractions were collected.

Fractions 10 through 21 were combined and evaporated to give 100 mg of 5-(thyroxinamide)pentyl, 4-methylumbelliferone, hydrogen phosphate, as a white microcrystalline solid, mp 191°–192° C. (darkens from 188° C.).

Analysis: Calculated for $C_{30}H_{29}I_4PH_2O_9 \cdot H_2O$: C, 32.22; H, 2.79; N, 2.50. Found: C, 32.37; H, 2.71; N, 2.46.

B. Assay method

The following reagents were assembled:

Reagent A: 50 mM Bicine buffer with 0.1% sodium azide, pH 8.5

Reagent B: 60 mM fenclofenac in 0.5N sodium hydroxide

Reagent C: thyroxine standards with concentrations of 0, 2, 4, 6, 8, 10, 12, 16 and 20 μg/dl prepared by adding thyroxine (Sigma) to thyroxine free serum.

Reagent D: antibody/enzyme reagent containing 50 μl antiserum per ml and 0.12 units per ml of phosphodiesterase (Sigma, Type VII) in Bicine buffer.

Reagent E: 1.24 μM of the labeled conjugate (Part A above) in 5 mM formate, 0.1% sodium azide buffer, pH 3.5.

The assay protocol involved adding 75 μl of Reagent B and 0.5 ml of Reagent A to a cuvette, followed by 75 μl of an appropriate Reagent C and another 0.5 ml of Reagent A, and finally 75 μl of Reagent D and a third 0.5 ml of Reagent A. After a 1 hour incubation at room temperature, the assay reaction was started by adding 75 μl of Reagent E and 0.5 ml of Reagent A to the cuvette. The fluorescence (excitation=360 nm, emission=450 nm) was measured 20 minutes after addition of Reagent E.

C. Results

The assay was run for each Reagent C and the results were as shown in Table 9.

TABLE 9

| thyroxine (μg/dl) | fluorescence units |
| --- | --- |
| 0 | 24.9 |
| 2 | 25.5 |
| 4 | 26.4 |
| 6 | 27.2 |
| 8 | 26.7 |
| 10 | 27.1 |
| 12 | 30.0 |
| 16 | 30.1 |
| 20 | 30.8 |

As thyroxine concentration increased, the fluorescence emission increased. Thus, an assay was established for thyroxine.

IX. The Use of Fenclofenac or Diclofenac in an Apoenzyme Reactivation Immunoassay System for Serum Thyroxine Standard curves for serum thyroxine were generated using a semiautomated assay protocol on the Gilford Clinical Chemistry Analyzer System 203-S (Gilford Instrument Laboratories, Oberline, OH, USA). The buffer comprised of 96 mM sodium phosphate, pH 7.0, 2.1 mM dichlorohydroxybenzene sulfonate (DHSA), 21 μg/ml peroxidase, 105 mM glucose and 2 mM sodium fenclofenac or sodium diclofenac was preheated to 37° C. before 0.8 ml were added to the reaction cup with 0.05 ml of 200 μl/ml thyroxine standards in $T_4$, $T_3$ free human serum (AMF Biological and Diagnostic Products, Sequin, TX, USA), 100 μl/ml anti(glucose oxidase) antiserum, 15 μl/ml anti(thyroxine) antiserum, 0.03M sodium phosphate, pH 7.0. The FAD-thyroxine conjugate (40 nM in 0.1M sodium phosphate, pH 7.0, 0.01% Triton X-100) as a 0.05 ml aliquot was added to the reaction cup and allowed to equilibrate for 30 seconds. The reaction was initiated by addition of 0.10 ml 1.0 μM apoglucose oxidase, 2 mM 4-aminoantipyrine, 12% glycerol, 80 mM sodium phosphate, pH 7.0. The absorbance at 520 nm was recorded after an 8 minute incubation.

TABLE 10

| Thyroxine Standard (μg/L) | Absorbance (with Fenclofenac) | Absorbance (with Diclofenac) |
| --- | --- | --- |
| 0 | 0.797 | 0.619 |
| 25 | 0.823 | 0.620 |
| 75 | 0.893 | 0.647 |
| 125 | 0.965 | 0.678 |
| 200 | 1.078 | 0.719 |

With fenclofenac or diclofenac as the iodothyronine dissociating agent, a correlation between the absorbance readout and the concentration of thyroxine in serum can be observed using a homogeneous apoenzyme reactivation immunoassay system.

X. Effect of pH on the Dissociation of Iodothyronine from Serum Proteins

Using the column procedure described in the second study in Example 1, the pH of the 0.1M sodium phosphate was varied and the concentration of the dissociating agent held constant at 2.0 mM. The columns were equilibrated with buffer containing the dissociating agent at the given pH and 165 μl of the serum diluted in buffer at the given pH (as described above) was applied to the column. The total counts were measured and then the columns were washed with buffer at the given pH. The counts remaining on the column represent the percentage of iodothyronine dissociated.

TABLE 11

| pH | Percent Dissociated by Fenclofenac | Percent Dissociated by Diclofenac |
| --- | --- | --- |
| 6.0 | 84 | 86 |
| 6.5 | 84 | 86 |
| 7.0 | 86 | 86 |
| 7.5 | 85 | 85 |
| 8.0 | 83 | 85 |

The dissociation of iodothyronine from serum proteins by fenclofenac or diclofenac is independent of pH (over the range 6.0–8.0) at which the incubation of the immunoassay is conducted.

XI. Preparation of Diclofenac

Following the method of Japanese Kokai patent document No. 80-79,352 (*Chem. Abs.* 94:121132u), 2-iodobenzoic acid was treated with thionyl chloride and dimethylamine to give N,N-dimethyl-2-iodophenylacetamide. Reaction upon heating with 2,6-dichloroaniline in the presence of potassium carbonate following the method of Japanese Kokai patent document No. 80-87,748 (*Chem. Abs.* 94:30378q) gave N,N-dimethyl-o-(2,6-dichlorophenylamino) phenylacetamide. Hydrolysis with 15% potassium hydroxide (British Pat. Appln. No. 2,027,028) gave diclofenac [o-(2,6-dichlorophenylamino)phenylacetic acid].

What is claimed is:

1. In a homogeneous competitive binding immunoassay method for determining an iodothyronine in a sample of unextracted serum or plasma, wherein a reaction mixture is formed by combining said sample with reagents comprising an antibody to said iodothyronine, a labeled iodothyronine conjugate, and a TBP blocking agent, and wherein a spectrophotometric response is generated in said reaction mixture at a wavelength greater than about 300 nm which is related to the concentration of said iodothyronine in said sample, the improvement which comprises employing a compound of the formula:

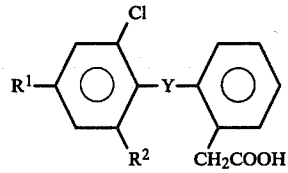

wherein Y is O or NH and one of $R^1$ and $R^2$ is chloro and the other is hydrogen, or a salt thereof, as said TBP blocking agent, which compound has substantially no absorption at wavelengths greater than 300 nm.

2. The method of claim 1 wherein said compound is 2-(2,4-dichlorophenoxy)phenylacetic acid or a salt thereof.

3. The method of claim 2 wherein 2-(2,4-dichlorophenoxy)phenylacetic acid or a salt thereof is present in the assay reaction mixture at a concentration greater than about 0.25M but less than that which substantially interfers with the assay.

4. The method of claim 2 wherein 2-(2,4-dichlorophenoxy)phenylacetic acid or a salt thereof is present in the assay reaction mixture at a concentration between about 0.25 mM and about 2.5 mM.

5. The method of claim 1 wherein said spectrophotometric response is a fluorescence emission.

6. The method of claim 5 wherein the intensity of said fluorescence emission is measured as a function of the amount of said iodothyronine in said sample.

7. The method of claim 6 wherein said labeled iodothyronine conjugate comprises a fluorescer.

8. The method of claim 1 wherein said spectrophotometric response is light absorption.

9. The method of claim 1 wherein said labeled conjugate comprises a participant in an enzymatic reaction producing a detectable product which generates said spectrophotometric response.

10. The method of claim 9 wherein said labeled iodothyronine conjugate comprises a fluorogenic enzyme substrate which releases a fluorescent product upon interaction with an enzyme, the ability of said enzyme to release such fluorescent product being altered by binding of said antibody with the labeled conjugate.

11. The method of claim 9 wherein said labeled iodothyronine conjugate comprises an enzyme prosthetic group which combines with an apoenzyme to produce an active enzyme whose activity is measured by its ability to catalyze a reaction producing a product having a characteristic fluorescen or absorbance at said wavelength greater than about 300 nm, the ability of said apoenzyme to combine with said prosthetic group in the labeled conjugate being altered by binding of said antibody with said labeled conjugate.

12. The method of claim 9 wherein said labeled iodothyronine conjugate comprises an enzyme which catalyzes a reaction producing a product having a characteristic fluorescence or absorbance at said wavelength greater than about 300 nm, the ability of said enzyme to catalyze such reaction being altered by binding of said antibody with said labeled conjugate.

13. The method of claim 9 wherein said labeled iodothyronine conjugate comprises an enzyme inhibitor which inhibits an enzyme whose activity is measured by its ability to catalyze a reaction producing a product having a characteristic fluorescence or absorbance at said wavelength greater than about 300 nm, the ability of said inhibitor to inhibit said enzyme being altered by binding of said antibody with said labeled conjugate.

14. The method of claim 1 wherein said iodothyronine is thyroxine (T-4).

15. The method of claim 1 wherein said iodothyronine is triiodothyronine (T-3).

16. The method of claim 11 wherein said enzyme prosthetic group is flavin adenine dinucleotide and said apoenzyme is apoglucose oxidase.

17. The method of any one of claims 1, 5, or 7 wherein said spectrophotometric response is at a wavelength less than about 700 nm.

18. In a test composition for the homogeneous competitive binding immunoassay determination of an iodothyronine in a blood sample, comprising an antibody to said iodothyronine; a labeled iodothyronine conjugate which has, as a detectable label property, the ability to generate a spectrophotometric response at a wavelength greater than about 300 nm, said detectable property being altered when the conjugate is bound with said antibody; and a TBP blocking agent, the improvement which comprises a compound of the formula:

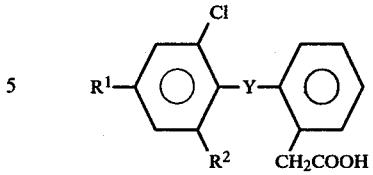

wherein Y is O or NH and one of $R^1$ and $R^2$ is chloro and the other is hydrogen, or a salt thereof, as a TBP blocking agent.

19. The test composition of claim 18 wherein said compound is 2-(2,4-dichlorophenoxy)phenylacetic acid or a salt thereof.

20. The test composition of claim 18 wherein said iodothyronine is thyroxine.

21. The test composition of claim 18 wherein said iodothyronine is triiodothyronine.

22. The test composition of claim 18 wherein said spectrophotometric response is a fluorescence emission.

23. The test composition of claim 22 wherein said labeled iodothyronine conjugate comprises a fluorescer.

24. The test composition of claim 18 wherein said spectrophotometric response is light absorption.

25. The test composition of claim 18 wherein said labeled conjugate comprises a participant in an enzymatic reaction producing a detectable product which generates said spectrophotometric response.

26. The test composition of claim 25 wherein said labeled iodothyronine conjugate comprises a fluorogenic enzyme substrate which releases a fluorescent product upon interaction with an enzyme, the ability of said enzyme to release such fluorescent product being altered by binding of said antibody with the labeled conjugate.

27. The test composition of claim 25 wherein said labeled iodothyronine conjugate comprises an enzyme prosthetic group which combines with an apoenzyme to produce an active enzyme whose activity is measured by its ability to catalyze a reaction producing a product having a characteristic fluorescence or absorbance at said wavelength greater than about 300 nm, the ability of said apoenzyme to combine with said prosthetic group in the labeled conjugate being altered by binding of said antibody with said labeled conjugate.

28. The test composition of claim 27 wherein said enzyme prosthetic group is flavin adenine dinucleotide and said apoenzyme is apoglucose oxidase.

29. The test composition of claim 25 wherein said labeled iodothyronine conjugate comprises an enzyme which catalyzes a reaction producing a product having a characteristic fluorescence or absorbance at said wavelength greater than about 300 nm, the ability of said enzyme to catalyze such reaction being altered by binding of said antibody with said labeled conjugate.

30. The test composition of claim 25 wherein said labeled iodothyronine conjugate comprises an enzyme inhibitor which inhibits an enzyme whose activity is measured by its ability to catalyze a reaction producing a product having a characteristic fluorescence or absorbance at said wavelength greater than about 300 nm, the ability of said inhibitor to inhibit said enzyme being altered by binding of said antibody with said labeled conjugate.

31. A test kit for the homogeneous competitive binding immunoassay determination of an iodothyronine in a sample of serum or plasma, comprising a packaged unit containing one or more containers holding:
(a) an antibody to said iodothyronine,
(b) a labeled iodothyronine conjugate which has, as a detectable label property, the ability to generate a spectrophotometric response at a wavelength greater than about 300 nm, said detectable property being altered when the conjugate is bound with said antibody, and
(c) a compound of the formula:

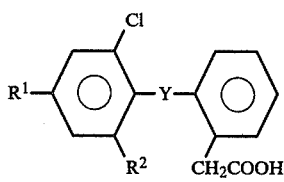

wherein Y is O or NH and one of R¹ and R² is chloro and the other is hydrogen, or a salt thereof, as a TBP blocking agent.

32. The test kit of claim 31 wherein said compound is 2-(2,4-dichlorophenoxy)phenylacetic acid or a salt thereof.

33. The test kit of claim 31 wherein said spectrophotometric response is a fluorescence emission.

34. The test kit of claim 33 wherein said labeled iodothyronine conjugate comprises a fluorescer.

35. The test kit of claim 31 wherein said spectrophotometric response is light absorption.

36. The test kit of claim 31 wherein said labeled conjugate comprises a participant in an enzymatic reaction producing a detectable product which generates said spectrophotometric response.

37. The test kit of claim 36 wherein said labeled iodothyronine conjugate comprises a fluorogenic enzyme substrate which releases a fluorescent product upon interaction with an enzyme, the ability of said enzyme to release such fluorescent product being altered by binding of said antibody with the labeled conjugate.

38. The test kit of claim 36 wherein said labeled iodothyronine conjugate comprises an enzyme prosthetic group which combines with an apoenzyme to produce an active enzyme whose activity is measured by its ability to catalyze a reaction producing a product having a characteristic fluorescence or absorbance at said wavelength greater than about 300 nm, the ability of said apoenzyme to combine with said prosthetic group in the labeled conjugate being altered by binding of said antibody with said labeled conjugate.

39. The test kit of claim 36 wherein said labeled iodothyronine conjugate comprises an enzyme which catalyzes a reaction producing a product having a characteristic fluorescence or absorbance at said wavelength greater than about 300 nm, the ability of said enzyme to catalyze such reaction being altered by binding of said antibody to said labeled conjugate.

40. The test kit of claim 36 wherein said labeled iodothyronine conjugate comprises an enzyme inhibitor which inhibits an enzyme whose activity is measured by its ability to catalyze a reaction producing a product having a characteristic fluorescence or absorbance at said wavelength greater than about 300 nm, the ability of said inhibitor to inhibit said enzyme being altered by binding of said antibody with said labeled conjugate.

41. The test kit of claim 31 wherein said iodothyronine is thyroxine (T-4).

42. The test kit of claim 31 wherein said iodothyronine is triiodothyronine (T-3).

43. A test device for the homogeneous competitive binding immunoassay determination of an iodothyronine in a blood sample, comprising the test composition of any one of claims 18–30 and a solid carrier member incorporated therewith.

44. The test kit of claim 38 wherein said enzyme prosthetic group is flavin adenine dinucleotide and said apoenzyme is apoglucose oxidase.

* * * * *